United States Patent
Bähnisch

(10) Patent No.: US 6,608,113 B1
(45) Date of Patent: Aug. 19, 2003

(54) METHOD AND INSTALLATION FOR SYNTHESISING METHANOL FROM HYDROGEN, CARBON MONOXIDE AND CARBON DIOXIDE UNDER PRESSURE

(75) Inventor: Hans-Joachim Bähnisch, Dortmund (DE)

(73) Assignee: Krupp Uhde GmbH, Dortmund (DE)

(*) Notice: Subject to any disclaimer, the term of this patent is extended or adjusted under 35 U.S.C. 154(b) by 0 days.

(21) Appl. No.: 09/830,856
(22) PCT Filed: Jul. 8, 2000
(86) PCT No.: PCT/EP00/06488
§ 371 (c)(1), (2), (4) Date: May 1, 2001
(87) PCT Pub. No.: WO01/17935
PCT Pub. Date: Mar. 15, 2001

(30) Foreign Application Priority Data

| Sep. 7, 1999 | (DE) | 199 42 559 |
| Oct. 23, 1999 | (DE) | 199 51 137 |
| Jan. 7, 2000 | (DE) | 100 00 280 |

(51) Int. Cl.[7] ............................................. C07C 27/00
(52) U.S. Cl. .................... 518/706; 518/702; 518/703; 518/704; 518/705
(58) Field of Search .................. 518/702, 703, 518/704, 705, 706

(56) References Cited

U.S. PATENT DOCUMENTS

| 2,904,575 A | 9/1959 | Peet |
| 4,226,795 A | * 10/1980 | Bowman ................ 210/449.5 |
| 5,252,609 A | * 10/1993 | Pinto ................ 518/703 |

FOREIGN PATENT DOCUMENTS

| DE | 2117060 | 4/1971 |
| DE | 2529591 | 1/1976 |
| DE | 3220995 | 12/1983 |
| DE | 3518362 | 11/1986 |
| DE | 4100632 | 4/1992 |

* cited by examiner

Primary Examiner—J. Parsa
(74) Attorney, Agent, or Firm—Collard & Roe, P.C.

(57) ABSTRACT

A process and a device are for the methanol synthesis from hydrogen, carbon monoxide and carbon dioxide under pressure, in particular for increasing the yield of processes already in use. Desulphurized natural gas is charged in a reformer and the synthesis gas is subsequently admitted to a methanol synthesis. There are the advantages that a favorable possibility for refitting existing plants is provided, and synthesis gas from external sources can be used. This is accomplished in the process in that after passing through the reformer, a side stream from the synthesis gas stream is supplied to a methanol pre-reactor. The methanol produced in the pre-reactor is supplied to the methanol stream exiting from the methanol synthesis of the main stream. A stream of synthesis gas non-reacted in the methanol pre-reactor is recycled into the main stream upstream of the methanol synthesis. An additional synthesis gas compensating the incurred loss is simultaneously charged within the zone of said feed into the main stream.

6 Claims, 3 Drawing Sheets

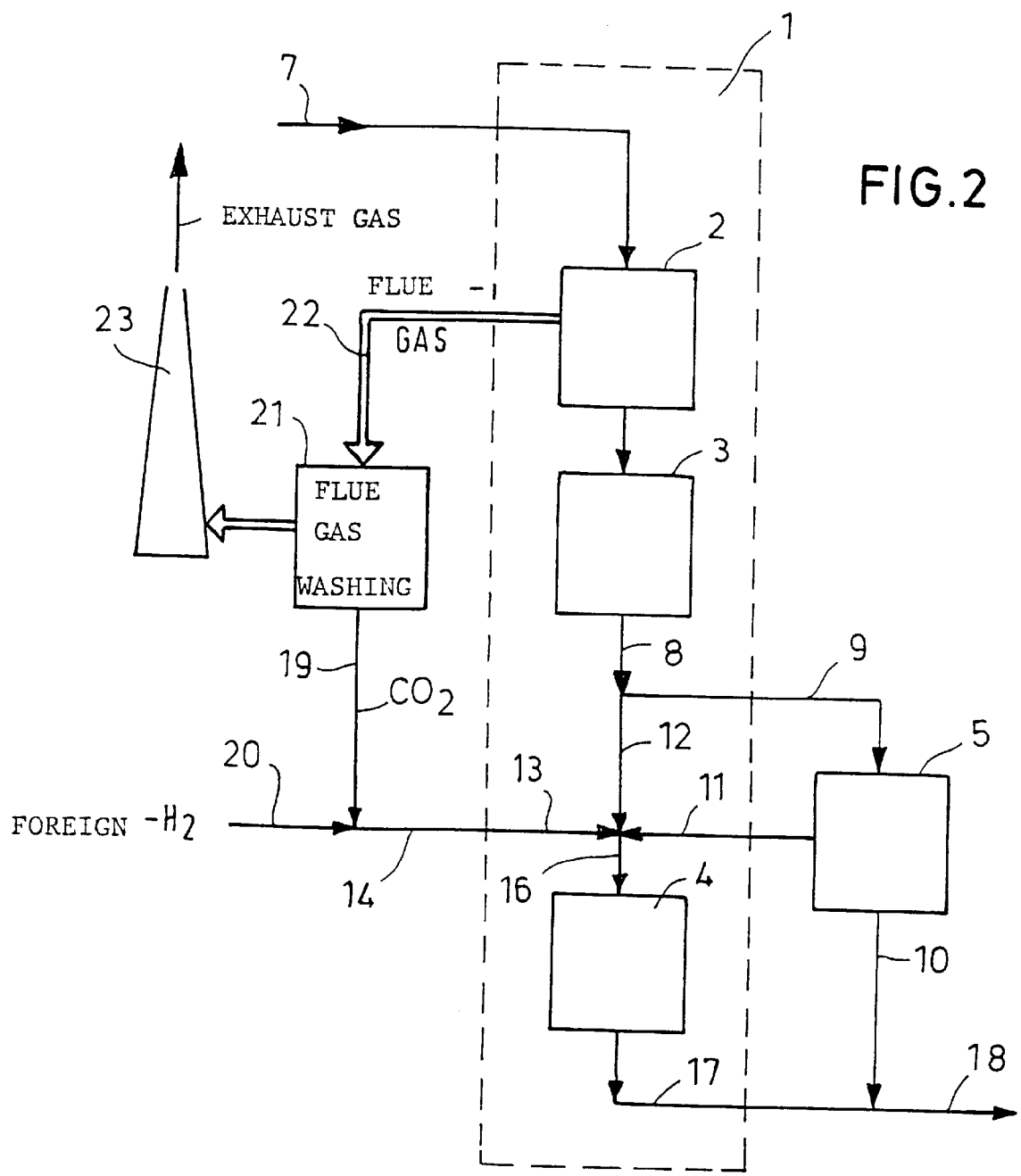

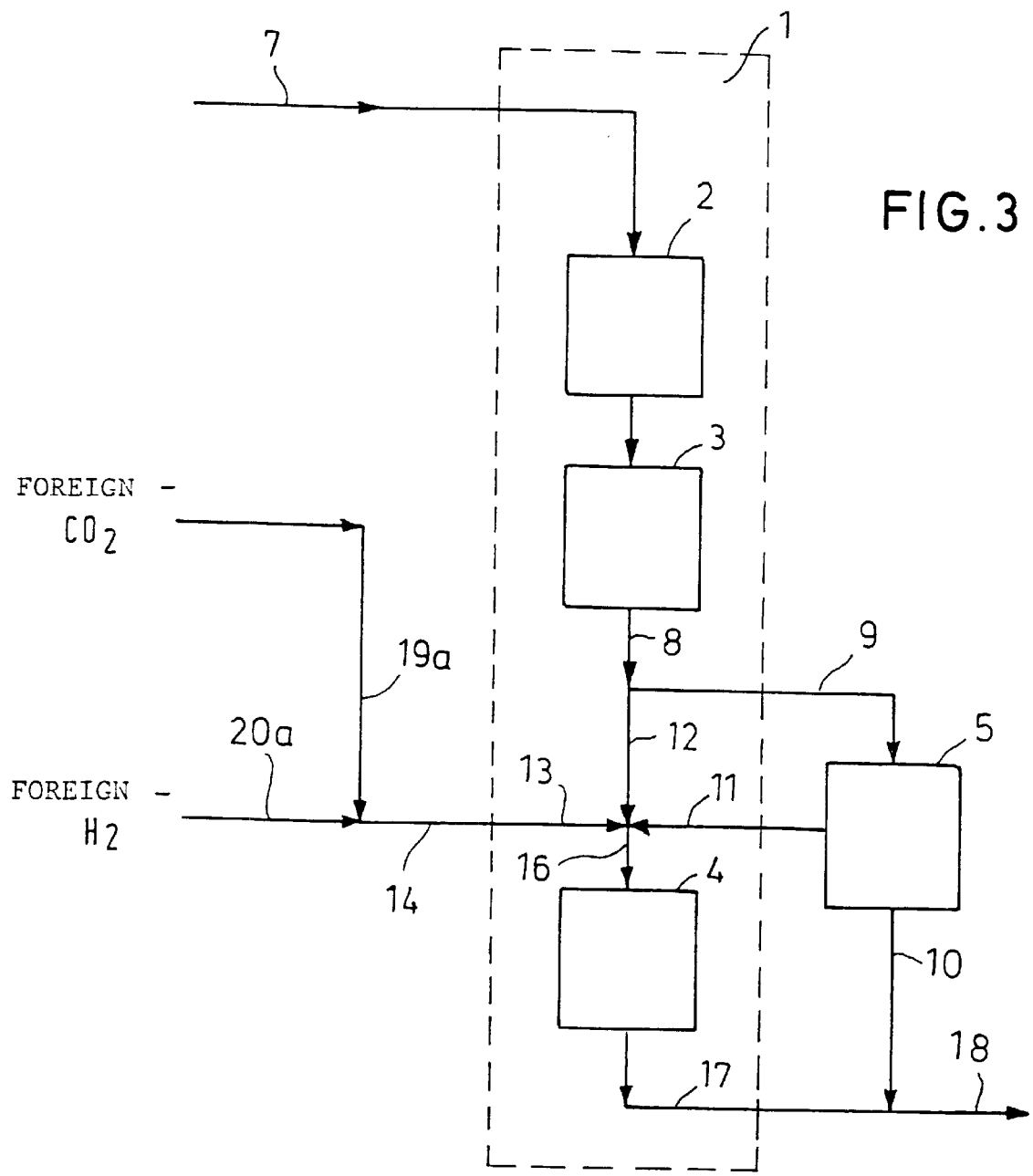

METHOD AND INSTALLATION FOR SYNTHESISING METHANOL FROM HYDROGEN, CARBON MONOXIDE AND CARBON DIOXIDE UNDER PRESSURE

CROSS REFERENCE TO RELATED APPLICATIONS

Applicant claims priorities under 35 U.S.C. §119 of German Application Nos. 199 42 559.0, filed: Sep. 7, 1999, 199 51 137.3, filed: Oct. 23, 1999, and 100 00 280.3, filed: Jan. 7, 2000. Applicant also claims priority under 35 U.S.C. §120 of PCT/EP00/06488, filed: Jul. 8, 2000. The international application under PCT article 21(2) was not published in English.

The invention relates to a process for the methanol synthesis from hydrogen, carbon monoxide and carbon dioxide under pressure, in particular for increasing the yield of processes already in use, whereby desulphurized natural gas is charged in a reformer and the synthesis gas is subsequently admitted to a methanol synthesis.

A number of devices or processes for the catalytic methanol synthesis are known, whereby the following documents are cited here as examples of the abundance of solutions: DE 21 17 060; De 25 29 591; DE 32 20 995; DE 35 18 362; U.S. Pat. No. 2,904,575; and DE 41 00 632.

A methanol production plant is normally operated in conjunction with a plant for producing synthesis gas, whereby both plants are dimensioned in such a way that the synthesis gas produced exactly covers the requirements of the methanol-producing catalyst of the synthesis gas circulation and in particular is stoichiometrically composed based on the following reactions, whereby only two of said reactions are linearly dependent upon each other:

$$CO + 2\ H_2 \longleftrightarrow CH_3OH - 90.84\ kJ/mol \quad (1)$$

$$CO_2 + H_2 \longleftrightarrow CO + H_2O + 41.20\ kJ/mol \quad (2)$$

$$CO_2 + 3\ H_2 \longleftrightarrow CH_3OH + H_2O - 49.64\ kJ/mol \quad (3)$$

According to the above reaction equations, the following applies to a stoichiometric synthesis gas:

$$\zeta = \frac{c_{H_2} - c_{CO_2}}{c_{CO} + c_{CO_2}} = 2 \quad (4)$$

whereby $c_i$ is the gas concentration of the respective starting materials based on moles.

The subscript "i" represents the individual compounds. Alternatively, $c_i$ can be written as set forth above, thus "$c_i$" can refer to: $c_{H_2}$, or $c_{CO_2}$, or $c_{CO}$, or $c_{CO_2}$.

Such a synthesis gas is usually produced in one single production line in a primary reformer, or together with a secondary reformer or in similar gas production equipment.

It is difficult to refit such a plant at a later time if existing production capacities have to be expanded. Generally, another production plant has to be built in such a case based on the layout of the old one, and no synergy effects can be expected. Furthermore, tying-in synthesis gas from external sources, which is often available at low cost when other larger plants are shut down, poses problems in that because of different compositions of the gas, which in most cases is an excessive component of carbon-containing compounds ("C-component"), such gas cannot be used for the production of methanol without further processing requiring substantial expenditure.

Therefore, the problem of the invention is to expand the known process by overcoming the drawbacks that have become known so far, creating good possibilities for later refitting of existing plants, and to make it possible to employ synthesis gas from other sources.

With a process of the type specified above, said problem is solved according to the invention in that after passing through the reformer, a side stream from the stream of synthesis gas is supplied to a methanol pre-reactor; the methanol produced in the pre-reactor is fed into the methanol stream exiting from the methanol synthesis of the main stream; and a stream of synthesis gas that has not been reacted in the methanol pre-reactor is recycled into the main stream prior to the methanol synthesis, whereby additional synthesis gas compensating the incurred loss is simultaneously charged within the zone where the non-reacted synthesis gas is recycled.

The methanol pre-reactor employed in the process, as well as the devices usually employed for conditioning the synthesis gas, as well as for the condensation and separation of the methanol produced can be refitted at a later time, whereby it is possible in this way to increase the production capacity up to 57% based on the capacity of the old installation. Of course, this concept is not limited to the later refitting of old plants, but it can be advantageously taken into account in the new conception as well.

Further developments of the invention follow from the dependent claims. Provision can be made in this conjunction for using as the additional synthesis gas a synthesis gas from external sources, i.e. from a separate synthesis gas source, or a synthesis gas that is withdrawn from the stream of natural gas as a bypass and then passed via an "autotherm" reformer, or a synthesis gas that originates from another synthesis gas production.

The foreign synthesis gas may originate in this connection from a combined "autotherm" reformer (also referred to as "CAR"), or from a reactor for partial oxidation, which can be refitted at a later time and is substantially more favorable in terms of construction than the apparatuses usually employed for producing synthesis gas with an exactly "fitting" gas composition. In this case, it becomes possible also jointly use a portion of the exhaust gas of the methanol production plant, which otherwise would be usable only as firing gas, as an additional gas charged in an "autotherm" reformer, or in a combined "autotherm" reformer.

It may be advantageous in this conjunction if the additional synthesis gas compensating the loss and fed into the main stream of the synthesis gas prior to the methanol synthesis, is withdrawn from a combined "autotherm" reformer and/or from a reactor for partial oxidation, or from another synthesis gas production, for which provision is made according to the invention as well.

According to another further development of the invention, the off-heat that has to be dissipated from the methanol pre-reactor during the cooling of the methanol synthesis gas mixture, is exploited for operating an absorption refrigeration machine. The produced cold is used for cooling the synthesis gas exiting from the reformers before it is compressed, so that compression energy is saved in this way.

The saved compression energy can be exploited according to the invention for compressing the synthesis gas obtained from external sources, or the additional synthesis gas produced in refitted reformers. Furthermore, the produced cold can be used for condensing out more methanol downstream of the methanol reactors. If the objective is to primarily save investment costs, and if the energy costs are low, it may be economical also to dispense with any exploitation of the off-heat and to employ instead of an absorption refrigeration machine a conventional refrigeration machine operated with, for example ammonia as the refrigerant.

With the mixture of the foreign synthesis gas and the synthesis gas obtained from the methanol pre-reactor after the methanol produced has been separated, it is necessary to ensure that the mixture approximately corresponding with the composition of the synthesis gas that has been originally branched off, fully covers the conditions for the existing methanol circulation, and that the original synthesis can be operated within the framework of the catalyst conditions. In order to assure this, at least the following must apply to the molar concentrations of the foreign synthesis gas: $0.8 \leq \zeta \leq 4$. An improvement is obtained if the following applies additionally: $1 \leq \zeta \leq 2.5$. The greater the proportion of the withdrawn side stream and the methanol produced in the pre-reactor, the more careful hone has to make sure that the characteristic $\zeta$ of the foreign synthesis gas approaches number 2.

A further development of the invention consists in that a mixture of $H_2$ and $CO_2$ is used as the additional synthesis gas, whereby the $CO_2$ present in the mixture originates from the flue gas of a firing installation or from the exhaust gas of a $CO_2$ washing operation in an ammonia plant (FIG. 2).

Using in the additional synthesis gas the $CO_2$ originating from a combustion process offers the great advantage that said $CO_2$ does not have to be discharged into the atmosphere, but is employed as intended for the synthesis.

Provision is made in this connection for the further development that the $CO_2$ from a flue gas purification plant originates from a firing operation, for example from the firing of the primary reformer.

Said procedure offers the additional benefit that the climatically active $CO_2$ is introduced into the substance circulation, so that a fee charged, for example for "hothouse emissions" needs no longer to be paid, which renders the procedure substantially more economical.

In addition to using the $CO_2$ from a combustion plant, such $CO_2$ may originate from the $CO_2$ washing operation of an $NH_3$ plant as well. Such an ammonia plant is not explained in greater detail in the following.

For solving the problem specified above, the invention makes provision also for a device for the methanol synthesis, in particular a device for carrying out the process according to any one of the preceding claims, such a device comprising a natural gas supply (or feed) line leading to a reformer, and a methanol synthesis connected downstream, whereby such a device as defined by the invention is characterized by the following:
  a branched-off line for a side stream of the synthesis gas exiting from the secondary reformer;
  a methanol pre-reactor in the side stream;
  a methanol feed line leading to the methanol main stream exiting from the methanol synthesis;
  a recycling line recycling non-reacted synthesis gas from the methanol pre-reactor into the synthesis gas main stream upstream of the methanol synthesis; as well as
  a feed line upstream of the methanol synthesis for feeding synthesis gas compensating losses.

As a further development of the invention, the device as defined by the invention is characterized in that an "autotherm" reformer is connected in parallel with the reformer, whereby the exiting synthesis gas is at least partly used as synthesis gas compensating losses.

According to the invention, provision can be made also for a flue gas washing operation for the flue gas exiting from the primary reformer, as well as for a $CO_2$ feed line for supplying the foreign or additional gas, as well as for a feed line for feeding foreign $H_2$ (FIG. 2), whereby it may be useful if provision is made for a supply line for feeding foreign $CO_2$ from a $CO_2$ washing operation in the $NH_3$ plant, as well as for a supply line for feeding foreign $H_2$, for which lines provision is made in further development of the invention as well.

Further details, advantages and features of the invention are contained in the following description and shown in the drawing. The drawing shows the following in a highly simplified manner:

BRIEF DESCRIPTION OF DRAWINGS

FIGS. 2 and 3 show modified examples of the block diagram in a comparative representation.

Figure 1:
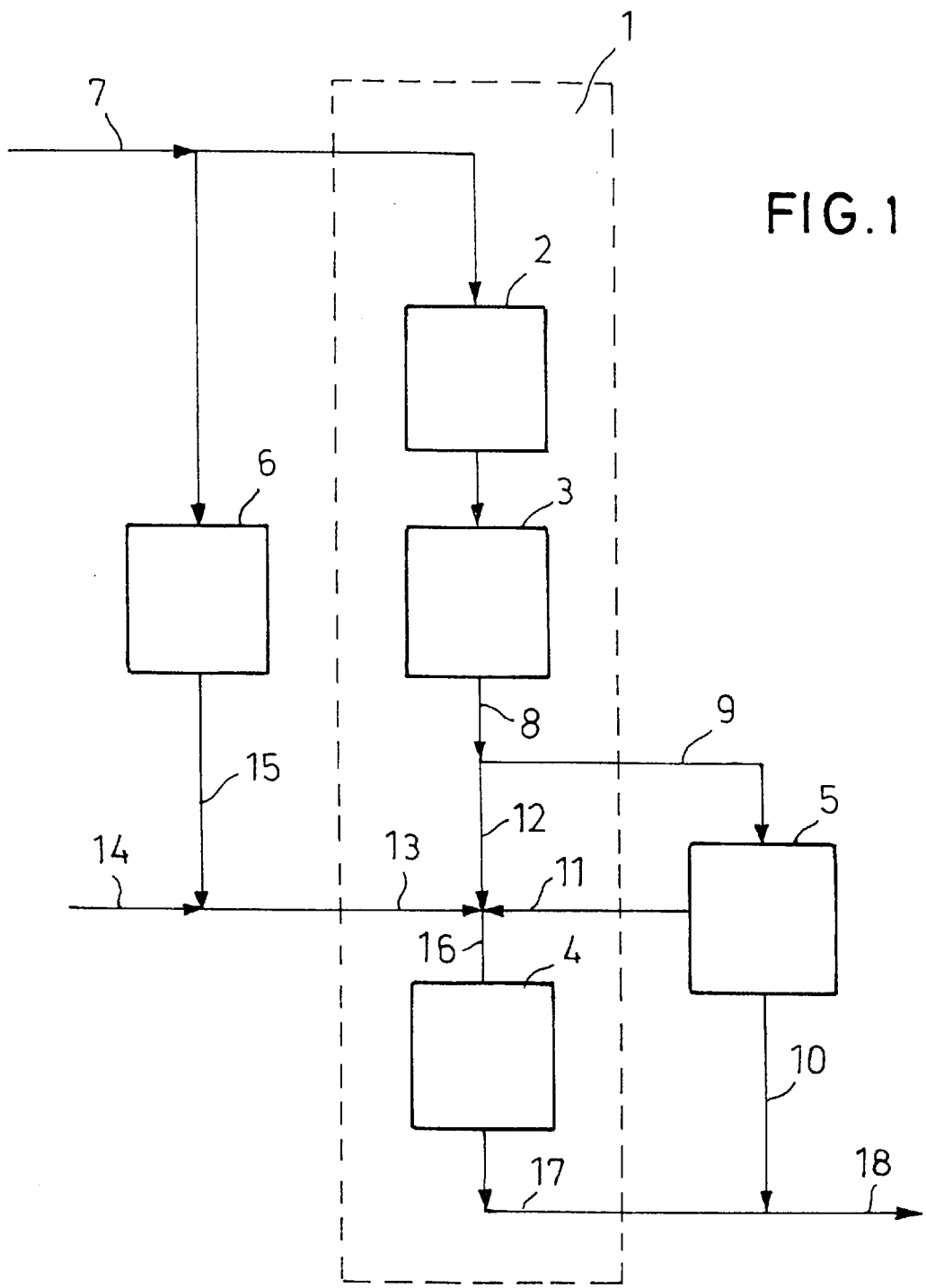
FIG. 1 is a block diagram of a device as defined by the invention.

The following is by way of example a description of the later refittability of a device 1, whereby the mode of operation is described at the same time.

A device 1 for producing methanol, which is already in operation and comprises a primary reformer 2, a secondary reformer 3 and a methanol synthesis 4, is additionally equipped at a later time with a methanol pre-reactor 5 and an "autotherm" reformer 6. The material charged is the desulphurized natural gas 7, which is passed into both the primary reformer 2 and the "autotherm" reformer 6, whereby other starting materials—which are not shown here—such as, for example steam and oxygen are added as well. A crude synthesis gas is produced from said starting materials in the primary reformer 2. Said crude synthesis gas substantially consists of hydrogen, carbon monoxide, carbon dioxide, and non-reacted steam and natural gas. The residual natural gas is reacted with oxygen in the secondary reformer 3 to hydrogen and carbon monoxide. The conditions in the primary reformer 2 and in the secondary reformer 3 are adjusted in this connection in such a way that a stoichiometric synthesis gas 8 according to the equations (1) to (4) is produced. A side stream 9 is branched off from said synthesis gas and supplied to the methanol pre-reactor 5. A portion of said synthesis gas is reacted in the methanol pre-reactor 5, condensed out, separated and discharged as the additional methanol 10. The remaining below-stoichiometric synthesis gas 11 is recycled, i.e. admixed again to the original main stream of the synthesis gas.

In order to avoid the formation of a below-stoichiometric mixture, the above-stoichiometric synthesis gas 13 is admixed to the main stream 12 of the synthesis gas as well. Said above-stoichiometric synthesis gas 13 consists of the foreign synthesis gas 14 and/or the additional synthesis 15, which has been produced only for that purpose in the refitted "autotherm" reformer 6, whereby the "autotherm" reformer 6 has to be understood as being an example only.

The stoichiometric synthesis gas 16 is formed with the admixtures added to the synthesis gas main stream 12. Said synthesis gas 16 has a composition equivalent to the stoichiometric synthesis gas 8. This means that a methanol 17 is produced in the conventional manner in the old methanol synthesis 4 which, together with the additional methanol 10, forms the new methanol product 18.

In modification of the device according to FIG. 1, FIG. 2 shows a device where foreign $CO_2$ and foreign $H_2$ are fed via the lines 19 and, respectively, 20 into the line 14 feeding the foreign synthesis gas. The $CO_2$ of the line 19 originates from a flue gas washing operation 21, which receives the flue gas from the primary reformer 2 via the supply line 22. The flue gas is purified in the flue gas washing plant 21 and the latter then feeds the $CO_2$ into the line 19, and feeds the exhaust gas into a smoke stack 23 indicated only symbolically. Said exhaust gas is obviously free of $CO_2$.

FIG. 3 shows the alternative, by which foreign $CO_2$ is supplied via the line 19a to the line 14 for the foreign synthesis gas, whereby said foreign $CO_2$ originates from the $CO_2$ washing operation of an ammonia plant not shown here in detail.

Foreign $H_2$ is supplied to the system via a line 20a in the present case as well.

It is obvious particularly in connection with the variation according to FIG. 2 that completely closed $CO_2$ circuits are possible, i.e. these plants operate in such a way that no $CO_2$ has to be discharged into the environment.

The following numerical example in table 1 serves for further illustration. It is assumed in this connection that an old plant for producing 1000 tons/day methanol exists and that its production capacity is to be expanded by about 35%. The numbers relate to the reference numerals in FIG. 1.

TABLE 1

| | | 8 | 9 | 10 | 11 | 12 | 13 | 16 | 17 | 18 |
|---|---|---|---|---|---|---|---|---|---|---|
| Quantity | [kmol/h] | 5147 | 3119 | | | | | | | |
| | [tons/day] | 1405 | 852 | | | | | | | |
| $H_2$ | [kmol/h] | 3550 | 2151 | 0 | 1215 | 1398 | 832 | 3446 | 0 | 0 |
| CO | [kmol/h] | 965 | 585 | 0 | 159 | 380 | 236 | 775 | 0 | 0 |
| $CO_2$ | [kmol/h] | 509 | 409 | 0 | 280 | 201 | 141 | 621 | 0 | 0 |
| $CH_4$ | [kmol/h] | 113 | 69 | 0 | 69 | 45 | 9 | 122 | 0 | 0 |
| $N_2$ | [kmol/h] | 5 | 3 | 0 | 3 | 2 | 2 | 7 | 0 | 0 |
| $H_2O$ | [kmol/h] | 5 | 3 | 0 | 2 | 2 | 0 | 4 | 0 | 0 |
| $\zeta$ | — | | 2.064 | 2.064 | | 2.129 | 2.064 | 1.837 | 2.023 | |
| $CH_3OH$ | [kmol/h] | 0 | 0 | 453 | 1 | 0 | 0 | 1 | 1302 | 1755 |
| | [tons/day] | | | 348 | 1 | | | 1 | 1000 | 1348 |

What is claimed is:

1. A process for methanol synthesis from hydrogen, carbon monoxide and carbon dioxide under pressure, comprising charging desulphurized natural gas in a primary reformer and synthesis gas is subsequently admitted to a methanol synthesis;

after passing through the primary and a secondary reformer, supplying a side stream from the synthesis gas stream to a methanol pre-reactor;

supplying the methanol produced in the pre-reactor to the methanol stream leaving from the main stream of the methanol synthesis; and recycling a synthesis gas stream not reacted in the methanol pre-reactor into the main stream prior to the methanol synthesis;

whereby an additional synthesis gas compensating the loss incurred is simultaneously charged within the zone where said unreacted synthesis gas stream is recycled.

2. The process according to claim 1, comprising using a foreign synthesis gas stream from a separate synthesis gas source or a synthesis gas originating from the natural gas stream charged as a bypass and passed via an "autotherm" reformer, or originating from another synthesis gas production as the additional synthesis gas.

3. The process according to claim 1, comprising withdrawing the additional synthesis gas compensating the loss and being supplied to the main synthesis stream prior to the methanol synthesis from a combined "autotherm" reformer and/or withdrawing from a reactor for partial oxidation or withdrawing from another synthesis gas production, the additional synthesis gas.

4. The process according to claim 1, comprising using off-heat of an additional methanol pre-reactor for operating an absorption refrigeration machine;

said machine producing cooling used for cooling a synthesis gas compression and/or unused compression energy is used for compressing foreign synthesis gas.

5. The process according to claim 1, comprising using a mixture of $H^2$ and $CO_2$ as the additional synthesis gas; and whereby the $CO_2$ present in the mixture originates from flue gas of a firing operation or from exhaust gas of a $CO_2$ washing operation in an ammonia plant.

6. The process according to claim 5, comprising the $CO_2$ originates from the flue gas purification plant of a firing operation, or the firing of the primary reformer.

* * * * *